(12) United States Patent
Karig et al.

(10) Patent No.: US 10,260,064 B2
(45) Date of Patent: Apr. 16, 2019

(54) PROGRAMMED DROPLET RUPTURE FOR DIRECTED EVOLUTION

(71) Applicant: The Johns Hopkins University, Baltimore, MD (US)

(72) Inventors: David K. Karig, Columbia, MD (US); Joshua T. Wolfe, Bethesda, MD (US)

(73) Assignee: The Johns Hopkins University, Baltimore, MD (US)

( * ) Notice: Subject to any disclaimer, the term of this patent is extended or adjusted under 35 U.S.C. 154(b) by 598 days.

(21) Appl. No.: 14/669,125

(22) Filed: Mar. 26, 2015

(65) Prior Publication Data

US 2016/0281081 A1    Sep. 29, 2016

(51) Int. Cl.
*C12N 15/10* (2006.01)

(52) U.S. Cl.
CPC ..... *C12N 15/1058* (2013.01); *C12N 15/1075* (2013.01)

(58) Field of Classification Search
None
See application file for complete search history.

(56) References Cited

U.S. PATENT DOCUMENTS

2006/0147909 A1* 7/2006 Rarbach ............ B01L 3/502784
                                                    435/6.14
2011/0275116 A1* 11/2011 Swartz ................ C12N 9/1029
                                                    435/41

OTHER PUBLICATIONS

Bodour et al. (Journal of Microbiological Methods 32 (1998) 273-280).*
Han et al. (Journal of applied microbiology 117.1 (2014): 139-150 published online Apr. 25, 2014).*
Karig et al. (Biotechnology and bioengineering 89.6 (2005): 709-718).*
Dusane et al. (Biotechnology and Genetic Engineering Reviews—vol. 27, 159-184 (2010)).*
Machado et al.( Metabolic engineering 14.5 (2012): 504-511).*
Zhu et al.( Journal of Bacteriology, May 2008, p. 3147-3154).*
Iyer et al.(PLoS One 8.10 (2013): e78442; 12 pages).*
Caiazza et al.( Journal of Bacteriology, Nov. 2005, p. 7351-7361). (Year: 2005).*

* cited by examiner

*Primary Examiner* — Tracy Vivlemore
*Assistant Examiner* — Sahana S Kaup
(74) *Attorney, Agent, or Firm* — Noah J. Hayward

(57) ABSTRACT

A method of directed evolution screening includes selecting a protein expression platform for an evolution target, expressing a key rupture gene configured to trigger droplet rupture, developing gene regulatory circuits to control expression of the key rupture gene as a function of performance of the evolution target, encapsulating expression components in droplets, and triggering droplet rupture by expressing a rupture agent from the key rupture gene.

16 Claims, 6 Drawing Sheets

PROGRAMMED DROPLET RUPTURE FOR DIRECTED EVOLUTION

TECHNICAL FIELD

Example embodiments relate generally to methods of directed evolution, and more particularly to methods of directed evolution screening using programmed droplet rupture.

BACKGROUND

Directed evolution has proved to be a powerful tool in protein engineering and synthetic biology. The most challenging part of directed evolution is typically the screening of mutants to assay for desired function. Many screening methods consist of simple binding assays, whereby a binding target is exposed to a mutant library, and mutants that do not wash away are selected. However, these assays are limited to the evolution of binding reagents, and a much wider space of applications is possible with directed evolution. For instance, it may be desirable to evolve gene circuits, genes for metabolic production of desired chemicals, genes for modifying or breaking down materials or chemicals, or components that regulate protein expression. Some of these applications have been addressed by other screening methods. These other screening methods have involved the expression of fluorescent or pigment proteins and subsequent screening based on fluorescence or color changes, use of fluorogenic or colorigenic enzyme substrates and subsequent screening based on fluorescence or color changes, expression of genes that regulate chemotaxis and subsequent screening based on spatial location of cells, or expression of genes that effect cell fitness and screening based on cell viability. In general, these methods are limited to either in vivo use or in vitro use, suffer from throughput or scalability issues, or lack broad applicability.

Therefore there remains a need in the art for methods of directed evolution screening that offer compatibility with in vivo and in vitro platforms (e.g. cells and cell-free systems), high throughput potential, scalability, and applicability to a broad range of different applications.

BRIEF SUMMARY

One or more embodiments of the invention may address one or more of the aforementioned problems. Certain embodiments according to the present invention provide a method of directed evolution screening suitable for a wide variety of applications. In accordance with certain embodiments, the method may comprise selecting a protein expression platform for an evolution target, expressing a key rupture gene configured to trigger droplet rupture, developing gene regulatory circuits to control expression of the key rupture gene as a function of performance of the evolution target, encapsulating expression components in droplets, and triggering droplet rupture by expressing a rupture agent from the key rupture gene.

BRIEF DESCRIPTION OF THE DRAWING(S)

Example embodiments of the present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
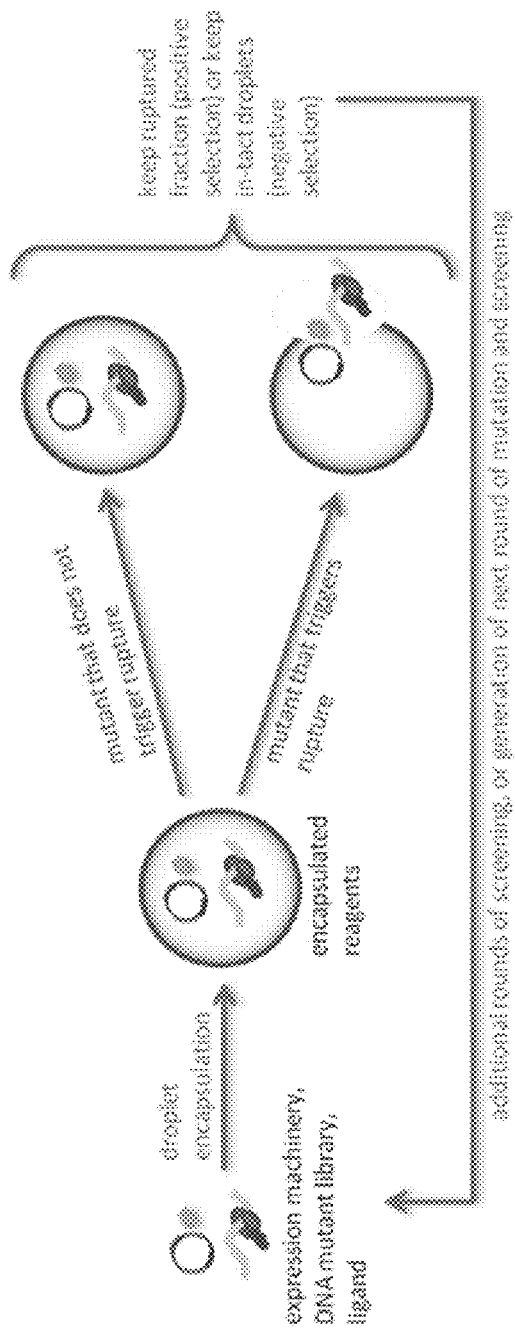
FIG. 1 illustrates an overview of directed evolution screening according to an example embodiment.

Some example embodiments now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

An example embodiment includes a method of directed evolution screening involving selecting a protein expression platform for an evolution target, expressing a key rupture gene configured to trigger droplet rupture, developing gene regulatory circuits to control expression of the key rupture gene as a function of performance of the evolution target, encapsulating expression components in droplets, and triggering droplet rupture by expressing a rupture agent from the key rupture gene in order to perform directed evolution screening based on the function of the mutation target being evolved.

The term "directed evolution", as used herein, may comprise any method used in protein engineering, genetic engineering or synthetic biology that mimics the process of natural selection to evolve proteins or nucleic acids toward a user-defined goal. As such, directed evolution may be used as an alternative to rationally designing modified proteins or nucleic acid sequences. The term "directed evolution screening", as used herein, may comprise expressing genetic variants and isolating those variants exhibiting a desired function.

The term "cell-free system", as used herein, may comprise an in vitro means of studying biological reactions that happen within cells while reducing the complex interactions found in a whole cell. To create cell-free systems, subcellular fractions may be isolated, for example, by ultracentrifugation to provide molecular machinery that can be used in reactions in the absence of many of the other cellular components. Cell-free systems may also be prepared, for instance, by mixing a number of purified enzymes and coenzymes. Cell-free systems may be advantageous, for example, because very high product yields are usually accomplished without the formation of by-products or the synthesis of cell mass. Additionally, cell-free systems may be able to implement some biological reactions that living organisms cannot perform. Also, cell-free systems may have faster reaction rates than living systems since all energy resources may be devoted to producing the desired RNA or proteins. Furthermore, cell-free synthesis products do not need to traverse a cell membrane to be available for analysis or activity at a desired location.

The term "evolution target", as used herein, may comprise any desired genetic variant (i.e., mutant) for which directed evolution screening is conducted. The term "protein expression platform", as used herein, may comprise any genetically manipulable live cells and/or any cell-free system used as a platform for producing proteins. The term "expression components", as used herein, may comprise cells and/or cell-free expression reagents. Expression components may comprise, for example, mutated versions of the gene of interest, the gene circuit controlling expression of the rupture agent, any inducers, any analytes, engineered DNA and/or the like. The term "key rupture gene", as used herein, may comprise any gene or set of genes implicated in triggering droplet rupture when expressed. The term "rupture agent", as used herein, may comprise any substance produced by live cells or cell-free systems capable of triggering droplet rupture.

The term "droplet", as used herein, may comprise a natural or synthetic material or chemical that encloses, encapsulates, and/or confines expression components. The term "rupture", as used herein, may comprise an act or process of releasing expression components from a droplet.

The term "biosurfactant", as used herein, may comprise amphiphilic compounds (e.g., rhamnolipids) that lower the surface tension on living surfaces (e.g., microbial cell surfaces) and/or permeabilize cell membranes. The term "dispersant", as used herein, may comprise any non-surface active polymer or surface-active substance that improves the separation of particles and, in this regard, prevents settling or clumping. Dispersants may comprise one or more surfactants and/or gases.

The term "rhamnolipid", as used herein, may comprise any of a class of glycolipids produced by various organisms (e.g. *Pseudomonas aeruginosa*) that functions as a bacterial surfactant. Rhamnolipid structure includes a glycosyl head group, in this case a rhamnose moiety, and a 3-(hydroxyalkanoyloxy)alkanoic acid (HAA) fatty acid tail. There are two main classes of rhamnolipids, mono-rhamnolipids and di-rhamnolipids, which comprise one or two rhamnose groups respectively. Rhamnolipids are also heterogeneous in the length and degree of branching of the HAA moiety. One example of a rhamnolipid (i.e., Rhamnolipid 1) is illustrated by Formula I:

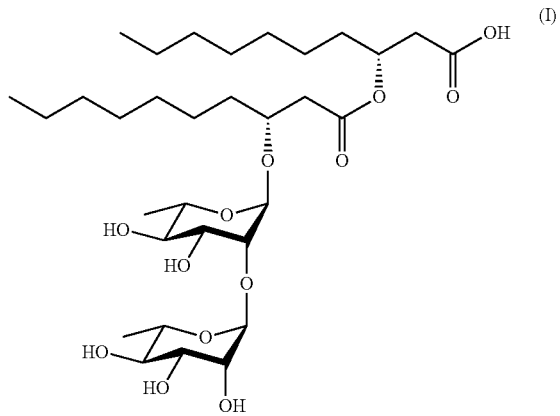

Rhamnolipids may be implicated in uptake of hydrophobic substrates, antimicrobial properties, virulence, biofilm development, and motility.

The term "perforin", as used herein, may comprise a cytolytic protein produced by the granules of immune cells such as Cytotoxic T lymphocytes (CTLs) and NK cells. Upon degranulation, perforin inserts itself into the target cell's plasma membrane, forming a pore. The term "perforin" used herein also more broadly refers to members of the membrane attack complex protein superfamily. The term "holin", as used herein, may comprise any one of a diverse group of small proteins produced by dsDNA bacteriophages in order to trigger and control the degradation of the host's cell wall at the end of the lytic cycle. Holins form pores in the host's cell membrane, allowing lysins to reach and degrade peptidoglycan, a component of bacterial cell walls. Holins have been shown to regulate the timing of lysis with great precision. Over 50 unrelated gene families encode holins, making them the most diverse group of proteins with common function. The term "lysin", as used herein, may comprise any one of a class of hydrolytic enzymes produced by bacteriophages in order to cleave the host's cell wall during the final stage of the lytic cycle. Lysins are highly evolved enzymes that are able to target one of the five bonds in peptidoglycan, the main component of bacterial cell walls, which allows the release of progeny virions from the lysed cell. In lysins, the N-terminal domain catalyses the hydrolysis of peptidoglycan, whereas the C-terminal domain binds to the cell wall substrate. The term "lysin" may also comprise any one of a class of hemolysins produced by bacteria and viruses. Many of these hemolysins are known to either disrupt membranes (e.g. delta-hemolysin) or to form pores in membranes (e.g. alpha-hemolysin). The term "antimicrobial peptide", as used herein, may comprise any one of a class of short, cationic, amphipathic peptides that can disrupt membrane bilayers.

The term "liposome", as used herein, may comprise a spherical, self-enclosed vesicle composed of amphipathic lipids. Liposomes may be used as vehicles for in vivo administration of agents, compositions, and compounds. Liposomes may comprise at least one closed lipid bilayer membrane, which defines an aqueous compartment. Liposomes have long been used for drug delivery by encapsulating water soluble agents within the internal aqueous compartment and/or water insoluble agents within the lipid bilayer. Liposomes may be unilamellar, having one lipid bilayer membrane, or multilamellar, having two or more concentrically arranged bilayers.

The term "polymersome", as used herein, may comprise any one of a class of artificial vesicles. Polymersomes may be made using amphiphilic synthetic block copolymers to form the vesicle membrane and may have radii ranging from 50 nm to 5 µm or more. Polymersomes may contain an aqueous solution in their core and may be useful for encapsulating and protecting sensitive molecules, such as drugs, enzymes, other proteins and peptides, DNA and RNA fragments and/or the like. The polymersome membrane may provide a physical barrier that isolates the encapsulated material from external materials.

The term "degradative enzyme", as used herein, may comprise any enzyme that degrades biological molecules (e.g., alginase). Examples of degradative enzymes may include lipase, carbohydrases, proteases, nucleases, or cathelicidins. The term "polymer-degrading enzyme", as used herein, may comprise any enzyme that degrades polymers (e.g., proteinase K).

In some example embodiments, a method of directed evolution screening having a wide variety of applications is provided. For instance, this method may provide, for example, a means of engineering aptamer biosensors;

designing proteins; improving the function of natural protein switches, altering or redirecting ligand binding targets or properties, and/or improving novel engineered proteins; improving protein specificity; improving key functional peptides, proteins, or metabolic enzymes; and/or optimizing function or production of an analyte or any compound that can be made by cells or cell-free systems. In general, methods of directed evolution screening according to certain example embodiments may include selecting a protein expression platform for an evolution target, expressing a key rupture gene configured to trigger droplet rupture, developing gene regulatory circuits to control expression of the key rupture gene as a function of performance of the evolution target, encapsulating expression components in droplets, and triggering droplet rupture by expressing a rupture agent from the key rupture gene. Droplet rupture may be triggered if performance of the evolution target is either satisfactory (positive selection) or unsatisfactory (negative selection). In certain embodiments, for example, the evolution target may be a rupture gene itself, in which case satisfactory performance is the act of droplet rupture. Alternately, in other embodiments, for instance, the evolution target may be any gene, in which case, satisfactory performance must be linked to expression of the rupture gene through regulatory circuits. In some embodiments, for example, performance of the evolution target may require external addition of chemical or biological agents. In such embodiments, for example, these external agents may be analytes (e.g., ligands and/or inducers) that are to be sensed by the evolution target. In certain embodiments, for instance, external agents may be encapsulated in the droplet or may be added externally following encapsulation and are able to diffuse into the droplet from the surrounding medium.

In accordance with an example embodiment, for instance, selecting a protein expression platform for an evolution target may comprise selecting at least one of cells or a cell-free system. In such embodiments, for example, the cells may comprise any prokaryotic or eukaryotic cells, including bacterial cells, yeast cells, plant cells, mammalian cells, insect cells, *Aspergillus niger* cells, *Aspergillus oryzae* cells, *Bacillus subtilis* cells, *Corynebacterium glutamicum* cells, *Lactococcus lactis* cells, *Mannheimia succiniciproducens* cells, *Micrococcus luteus* cells, *Streptomyces coelicolor* cells, or *Schizosaccharomyces pombe* cells. In certain embodiments, for instance, the cells may comprise *Escherichia coli* cells, *Saccharomyces cerevisae* cells, wheat germ cells, reticulocyes, HeLa cells, *Spodoptera frugiperda* cells, *Trichoplusia ni* cells, *Aspergillus niger* cells, *Aspergillus oryzae* cells, *Bacillus subtilis* cells, *Corynebacterium glutamicum* cells, *Lactococcus lactis* cells, *Mannheimia succiniciproducens* cells, *Micrococcus luteus* cells, *Streptomyces coelicolor* cells, or *Schizosaccharomyces pombe* cells. In some embodiments, for instance, any live cells capable of being genetically manipulated may be used.

According to an example embodiment, the cell-free system may comprise a cell-free system prepared from any prokaryotic or eukaryotic cells including bacteria, yeast, plant cells, mammalian cells, or insect cells. In certain embodiments, for example, the cell-free system may comprise a cell-free system prepared from *Escherichia coli* cells, *Saccharomyces cerevisae* cells, wheat germ cells, reticulocyes, HeLa cells, *Spodoptera frugiperda* cells, or *Trichoplusia ni* cells. In such embodiments, for instance, the cell-free system may comprise components of *Escherichia coli* cells, *Saccharomyces cerevisea* cells, wheat germ cells, reticulocyes, HeLa cells, *Spodoptera frugiperda* cells, or *Trichoplusia ni* cells.

In accordance with an example embodiment, expressing a key rupture gene configured to trigger droplet rupture may comprise expressing a gene or set of genes configured for alcohol production. In some embodiments, for example, expressing a gene configured for alcohol production may comprise expressing a gene (or set of genes) configured for linear higher alcohol production. In further embodiments, for instance, expressing a gene configured for alcohol production may comprise expressing a gene (or set of genes) configured for octanol production. In such embodiments, for example, expressing a key rupture gene configured to trigger droplet rupture may comprise expressing a gene (or set of genes) configured for octanol production in conjunction with *Escherichia coli* cells and/or *Escherichia coli* extracts as a protein expression platform for an evolution target. In other embodiments, for example, alcohol production may be placed under control of gene regulatory elements in any expression system. In this regard, for instance, controlled droplet rupture may be triggered under specific conditions determined by directed evolution criteria.

According to an example embodiment, expressing a key rupture gene configured to trigger droplet rupture may comprise expressing a gene (or set of genes) configured for biosurfactant and/or dispersant production. In some embodiments, for example, expressing a gene configured for biosurfactant and/or dispersant production may comprise expressing a gene (or set of genes) configured for rhamnolipid production. In certain embodiments, for instance, the gene expressed may comprise a gene essential for rhamnolipid production in *Pseudomonas aeruginosa*. In such embodiments, for example, the gene may comprise at least one of rhlA, rhlB, or rhlC. In further embodiments, for instance, the gene may comprise at least one of rhlA or rhlB in conjunction with *Escherichia coli* cells and/or *Escherichia coli* extracts as a protein expression platform for an evolution target. In this regard, for example, the ability of rhamnolipids to direct detachment from biofilms and permeabilize cell membranes of certain bacteria may be harnessed for droplet rupture in conjunction with droplets that have similar chemical properties to cell membranes. Thus, expression of rhamnolipids may become an efficient screening method for specific gene function.

According to an example embodiment, expressing a gene configured to trigger droplet rupture may comprise expressing at least one of performs, holins, lysins, antimicrobial peptides or other membrane proteins. In some embodiments, for instance, expressing at least one of performs, holins, lysins, or antimicrobial peptides may comprise expressing alpha-hemolysin in conjunction with expression components that are encapsulated in liposomes. In certain embodiments, for instance, expressing alpha-hemolysin may disrupt the entire liposome, resulting in droplet rupture. In other embodiments, for example, membrane proteins may functionally integrate into liposome preparations. In this regard, for instance, membrane proteins may stabilize the droplet against rupture, allowing us to use negative selection to screen for membrane proteins with desirable membrane enhancing properties. In other embodiments, for example, integrated membrane proteins may have additional gene regulatory functions that govern rupture gene expression, allowing the use of droplet rupture to screen for membrane-bound biosensor function.

According to an example embodiment, expressing a gene configured to trigger droplet rupture may comprise expressing at least one degradative enzyme in conjunction with expression components that are encapsulated in a polysaccharide. In some embodiments, for example, at least one degradative enzyme may comprise alginase (i.e., alginate lyase) and the polysaccharide may comprise alginate. In this regard, for instance, to trigger release from encapsulation, alginase may be expressed in response to meeting target criteria for directed evolution to break down alginate.

According to an example embodiment, expressing a gene configured to trigger droplet rupture may comprise expressing a protease and/or a peptidase in conjunction with expression components that are encapsulated in peptide surfactant vesicle structures. In some embodiments, for example, expressing a gene configured to trigger droplet rupture may comprise expressing a protease in conjunction with expression components that are encapsulated in peptide surfactant vesicle structures. In other embodiments, for instance, expressing a gene configured to trigger droplet rupture may comprise expressing a peptidase in conjunction with expression components that are encapsulated in peptide surfactant vesicle structures.

According to an example embodiment, expressing a gene configured to trigger droplet rupture may comprise expressing at least one polymer-degrading enzyme in conjunction with expression components that are encapsulated in polymersomes. In some embodiments, for example, the expression components may be encapsulated in PLA-based polymersomes. In such embodiments, for instance, proteinase K may be expressed in order to destabilize the PLA-based polymersomes.

According to an example embodiment, mutant libraries may be generated. In such embodiments, mutant libraries may be used along with gene regulatory circuits to isolate a desired functionality. In certain embodiments, error prone polymerase chain reactions, site directed mutagenesis, base pair insertion or deletion, and/or DNA shuffling may be used to generate libraries of candidate mutants for screening.

In accordance with an example embodiment, developing gene regulatory circuits may comprise developing a positive selection scheme or a negative selection scheme. In some embodiments, for instance, inverting gene circuits may be incorporated to facilitate the use of alternative selection strategies. In certain embodiments, for example, developing a positive selection scheme may comprise triggering rupture in response to the evolution target exhibiting a desired functionality. In such embodiments, for instance, a positive selection scheme may allow the screened evolution target to be immediately accessible for subsequent rounds of evolution and/or re-encapsulation with different analytes and inducers to screen for different conditions.

According to an example embodiment, developing a negative selection scheme may comprise avoiding rupture in response to the evolution target exhibiting a desired functionality. In such embodiments, for example, a negative selection scheme may allow droplets to be available for additional analysis. In certain embodiments, for instance, additional analysis may comprise analyzing expression of different fluorescent proteins. In further embodiments, for example, RNA-based regulation may be used in response to a desire for faster control. In other embodiments, for instance, gene circuits may be engineered to produce a more binary output (e.g., through the use of positive feedback).

In accordance with an example embodiment, encapsulating expression components in droplets may comprise encapsulating at least one of cells or cell-free systems in droplets. In certain embodiments, for example, encapsulating expression components in droplets may comprise creating a single emulsion. In such embodiments, for instance, a dispersed phase may comprise the expression components, and a continuous phase may comprise, for example, a mixture of oil and surfactant. In other embodiments, for example, encapsulating expression components in droplets may comprise creating a double emulsion. In some embodiments, for instance, the double emulsion may comprise a water-in-oil-in-water (i.e., W/O/W) emulsion having an inner phase, a middle phase, and an outer phase. In such embodiments, for example, the inner phase may comprise the expression components, the middle phase may comprise oil, and the outer phase may comprise an aqueous solution that may contain, for example, buffers, salts, and/or nutrients. In certain embodiments, for instance, the droplets may comprise alginate beads. In such embodiments, for example, the inner phase may comprise at least one of expression components or alginate, the middle phase may comprise oil, and the outer phase may comprise reagents for crosslinking alginate (e.g., calcium chloride or barium chloride). In further embodiments, for instance, the droplets may comprise polymersomes. In such embodiments, for example, the inner phase may comprise expression components, the middle phase may comprise at least one of diblock copolymers or homopolymers, and the outer phase may comprise alcohols and/or salts.

According to an example embodiment, microfluidic devices may be used to encapsulate expression components. In certain embodiments, for instance, a T-junction device may be used to encapsulate expression components. In other embodiments, for example, an X-junction device may be used to encapsulate expression components. In further embodiments, for instance, a flow-focusing device may be used to encapsulate expression components.

According to an example embodiment, droplets may be generated using an electric field. In certain embodiments, for example, droplets may be generated using pressure regulation. In further embodiments, for instance, liposome droplets may be generated using extrusion devices.

In accordance with an example embodiment, the method may further comprise identifying rupture efficiency and timing for varying expression strengths of the rupture agent. In such embodiments, for example, identifying rupture efficiency and timing for varying expression strengths of the rupture agent may comprise placing the key rupture gene under control of an induction system. In some embodiments, for instance, the induction system may comprise an inducible cell-free negative feedback circuit that functions in both live cells and in cell-free systems. In such embodiments, for example, adding an inducer (e.g., anhydrotetracycline) may cause an increase in expression of a target gene. In certain embodiments, for instance, after placing a rupture gene under inducible control, different concentrations of inducer may be added, and the percentage of ruptured droplets over time may be characterized for each inducer concentration. In this regard, for example, initial optimization of conditions for controlled rupture may occur, and carefully tuned induction of the rupture gene can be used to set baseline levels of the rupture gene (e.g., in aptamer and protein switches).

In accordance with an example embodiment, the method may be used for various applications. For example, in certain embodiments, the method may be used for at least one of engineering aptamer biosensors; designing proteins; improving the function of natural protein switches; improving protein specificity; improving key functional peptides, proteins, or metabolic enzymes; and/or optimizing production of an analyte or any other compound that can be produced by cells or cell-free systems. In certain embodiments, for instance, the method may be used for engineering aptamer biosensors. In such embodiments, for example, riboswitches that silence translation in the absence of chosen analytes may be developed, and aptamer sequences would be expressed upstream of a short, random DNA sequence constituting the 5' UTR of the rupture gene. In this regard, for instance, through multiple rounds of positive selection, negative selection, or alternations of positive and negative selection, the resulting DNA encoding improved riboswitches may be used to generate another round of mutants or may be cloned, purified, sequenced, and further analyzed.

According to an example embodiment, the method may be used to design proteins. In such embodiments, for example, the method may be used to design allosteric regulators, periplasmic binding proteins, membrane proteins (e.g., G-protein coupled receptors) and/or the like. In certain embodiments, for instance, the method may be used to improve the function of natural protein switches, alter or redirect ligand binding targets or properties, and/or improve novel engineered proteins. In such embodiments, for example, a key rupture gene or genes may be expressed under the control of a promoter that is regulated by a target protein switch. In this regard, for instance, through multiple rounds of positive selection, negative selection, or alternations of positive and negative selection, protein switches that exhibit a strong response to ligand addition may be evolved. According to an example embodiment, the method may be used to improve protein specificity. In such embodiments, for example, if a protein switch responds to two different ligands, only one of which is desirable, positive selection may be used to retain and/or improve the response to the desirable ligand, while negative selection may be performed to reduce the response to the undesirable ligand.

According to an example embodiment, the method may be used to improve key functional peptides, proteins, or metabolic enzymes. In such embodiments, for instance, enzyme mutants that more efficiently degrade a target may be selected. In other embodiments, for example, key metabolic pathway mutants may be selected in order to optimize synthesis of a product. In further embodiments, for instance, mutants that more efficiently produce biosurfactants and dispersants may be selected to allow for directed evolution of these target molecules. In certain embodiments, for example, protease mutants that more efficiently cleave peptide surfactants may be selected, and perforin, holin, or lysin mutants that more efficiently disrupt liposomes may be selected. In other embodiments, for instance, a polymersome platform may be used to identify and/or optimize components (e.g., proteins, enzymes) or whole strains that can break down an enclosing polymer.

According to an example embodiment, the method may be used to optimize production of an analyte. In such embodiments, for example, riboswitches, protein switches, or other regulator switches capable of sensing a target analyte may be harnessed in order to optimize production of the analyte. In certain embodiments, for instance, mutant metabolic pathways may be screened for production of a target compound. In such embodiments, for example, successful mutants that produce high amounts of the compound may trigger stronger activation of aptamer or protein switches, which may regulate droplet rupture genes.

For example, FIG. 1 illustrates an overview of directed evolution screening according to an example embodiment. As shown in FIG. 1, expression machinery, DNA mutant libraries, ligands and/or the like are encapsulated in droplets to form encapsulated reagents. Alternatively, in some embodiments, ligands may be added externally following encapsulation. In a "negative selection" case, mutants in the encapsulated reagents that do not trigger droplet rupture are collected and used for additional rounds of screening, generation of another round of mutation and screening, or potentially final analysis and application. In a "positive selection" case, mutants that trigger droplet rupture are collected from ruptured fractions and used for additional rounds of screening, generation of another round of mutation and screening, or potentially final analysis and application.

Figure 2A:
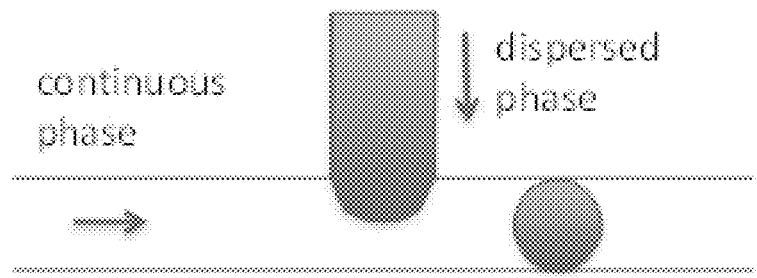
FIGS. 2A-2D illustrate various encapsulation methods in accordance with example embodiments.
Figure 2B:
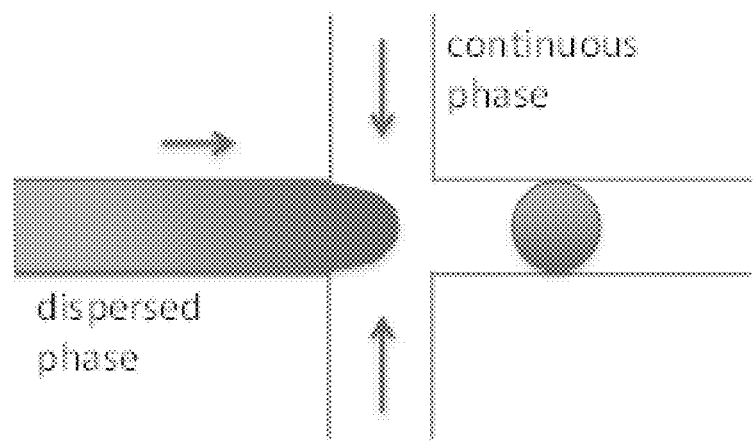
Figure 2C:
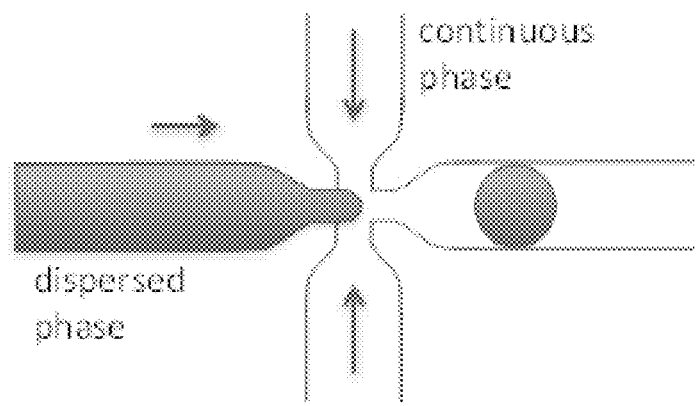
Figure 2D:
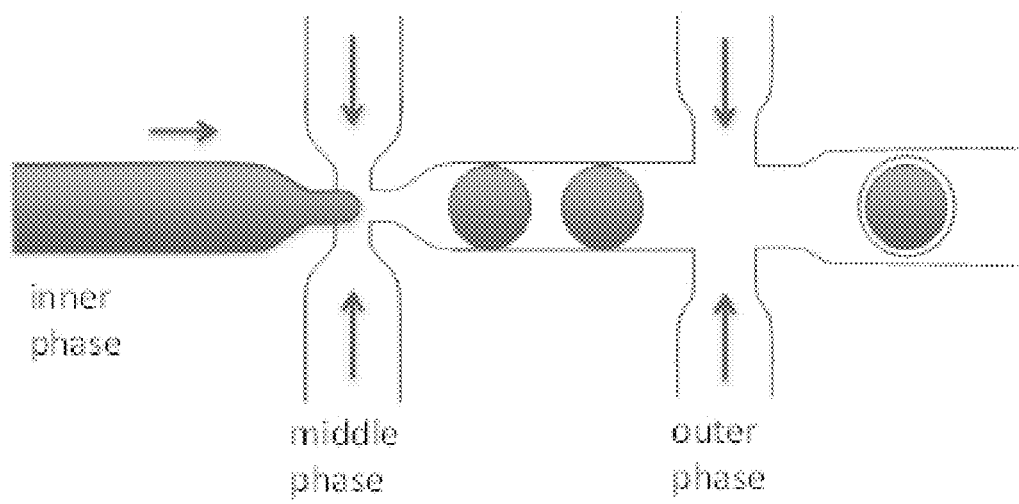

FIGS. 2A-2D, for example, illustrate various encapsulation methods in accordance with example embodiments. As shown in FIG. 2A, a T-junction microfluidic device may be used to encapsulate expression components. As shown in FIG. 2B, an X-junction microfluidic device may be used to encapsulate expression components. As shown in FIG. 2C, a flow-focusing microfluidic device may be used to encapsulate expression components. As shown in FIG. 2D, combinations of any of the microfluidic devices illustrated in FIGS. 2A-2C may be used to create double emulsions to encapsulate expression components.

Figure 3:
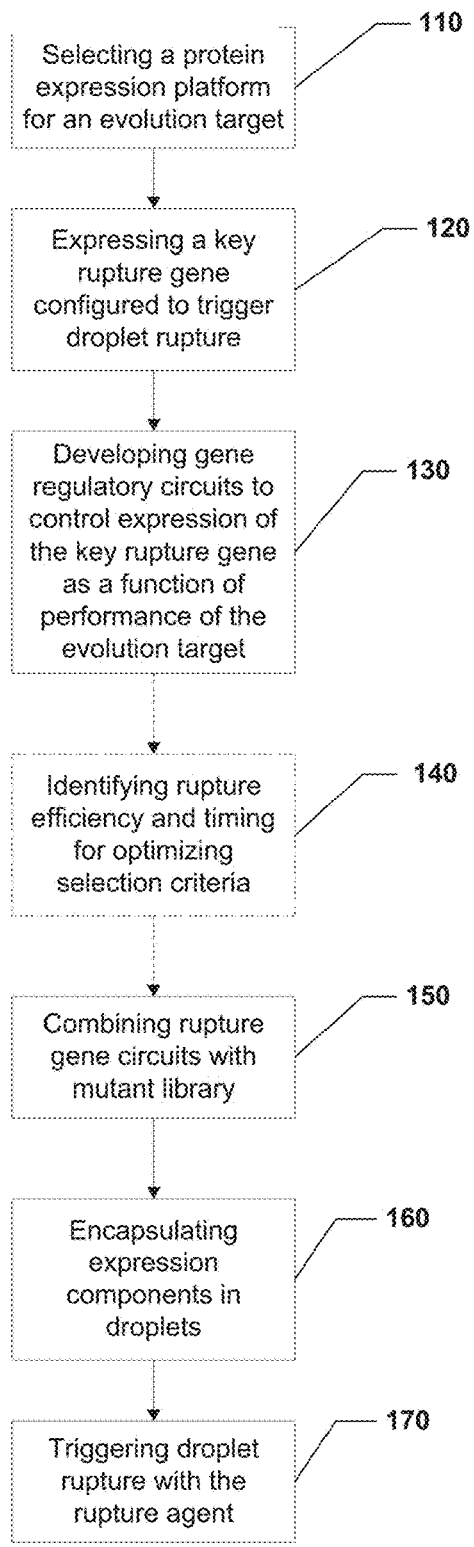
FIG. 3 illustrates a block diagram of a method of directed evolution screening according to an example embodiment.

FIG. 3, for example, illustrates a block diagram of a method of directed evolution screening according to an example embodiment. As shown in FIG. 3, the method comprises selecting a protein expression platform for an evolution target at operation 110. The method further comprises expressing a key rupture gene configured to trigger droplet rupture at operation 120, developing gene regulatory circuits to control expression of the key rupture gene as a function of performance of the evolution target at operation 130, combining rupture gene circuits with the mutant library at operation 150, encapsulating expression components in droplets at operation 160, and triggering droplet rupture with the rupture agent at operation 170. The method may further comprise an optional operation 140, which comprises identifying rupture efficiency and timing for varying expression strengths of a rupture agent in order to optimize selection criteria.

Figure 4:
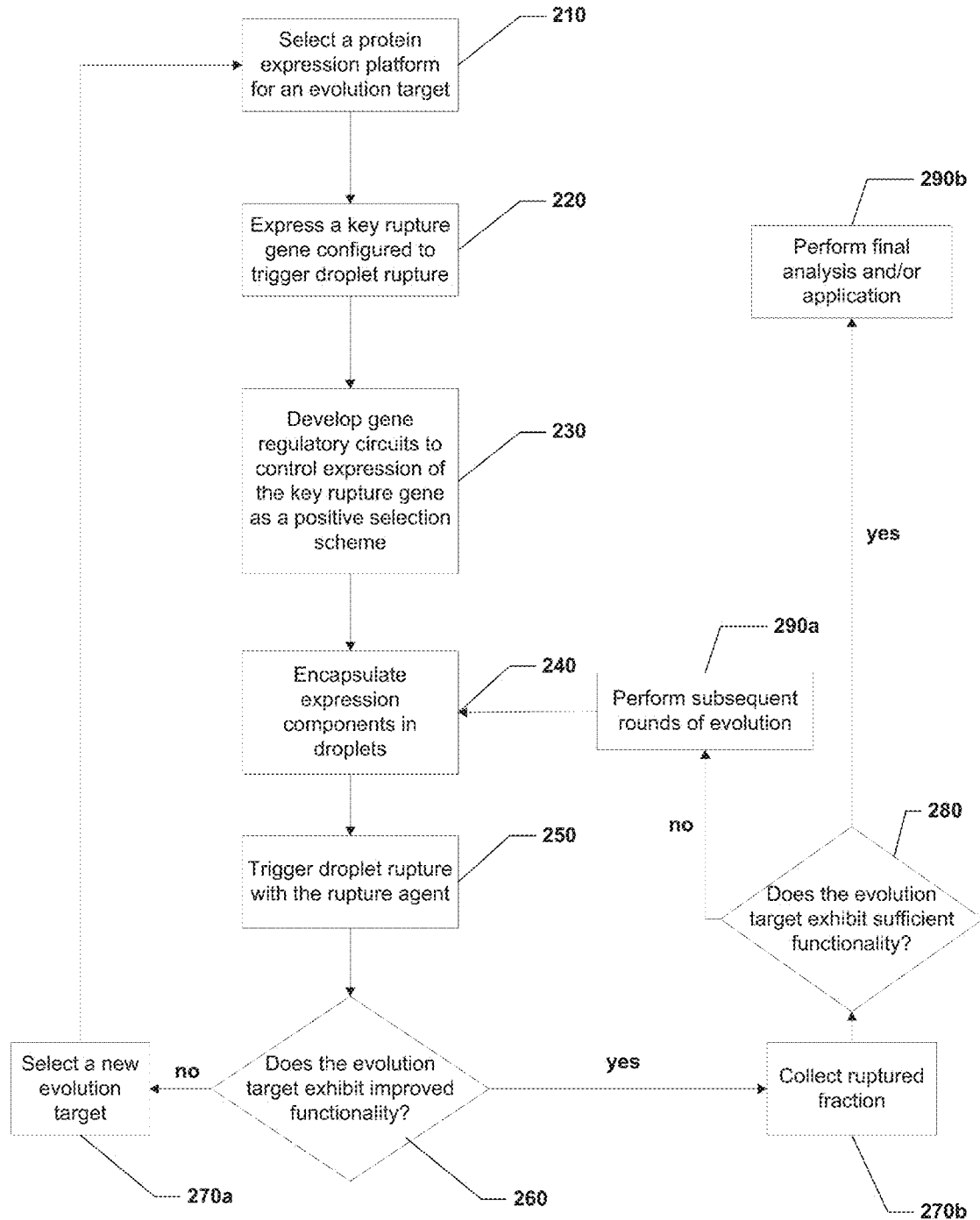
FIG. 4 illustrates a control flow diagram of a positive selection scheme according to an example embodiment.

FIG. 4, for example, illustrates a control flow diagram of a positive selection scheme according to an example embodiment. As shown in FIG. 4, operation may begin by selecting a protein expression platform for an evolution target at operation 210. The operation may continue at operation 220 by expressing a key rupture gene configured to trigger droplet rupture. The operation may continue by developing gene regulatory circuits to control expression of the key rupture gene as a positive selection scheme at operation 230. The operation may continue at operation 240 by encapsulating expression components in droplets. The operation may continue by triggering droplet rupture with the rupture agent at operation 250. The operation may continue at operation 260 by making a decision as to whether the evolution target exhibits improved functionality. If the decision is made that the evolution target does not exhibit improved functionality, then a new evolution target is selected at operation 270a, and the positive selection scheme will begin again starting at operation 210. If the decision is made that the evolution target does exhibit improved functionality, then ruptured fractions will be collected at operation 270b. The operation may continue at operation 280 by making a decision as to whether the evolution target exhibits sufficient functionality. If the evolution target does not exhibit sufficient functionality at 280, subsequent rounds of evolution may be performed as indicated at operation 290a. If the evolution target exhibits sufficient functionality at operation 280, final analysis and/or application may be performed at operation 290b.

Figure 5:
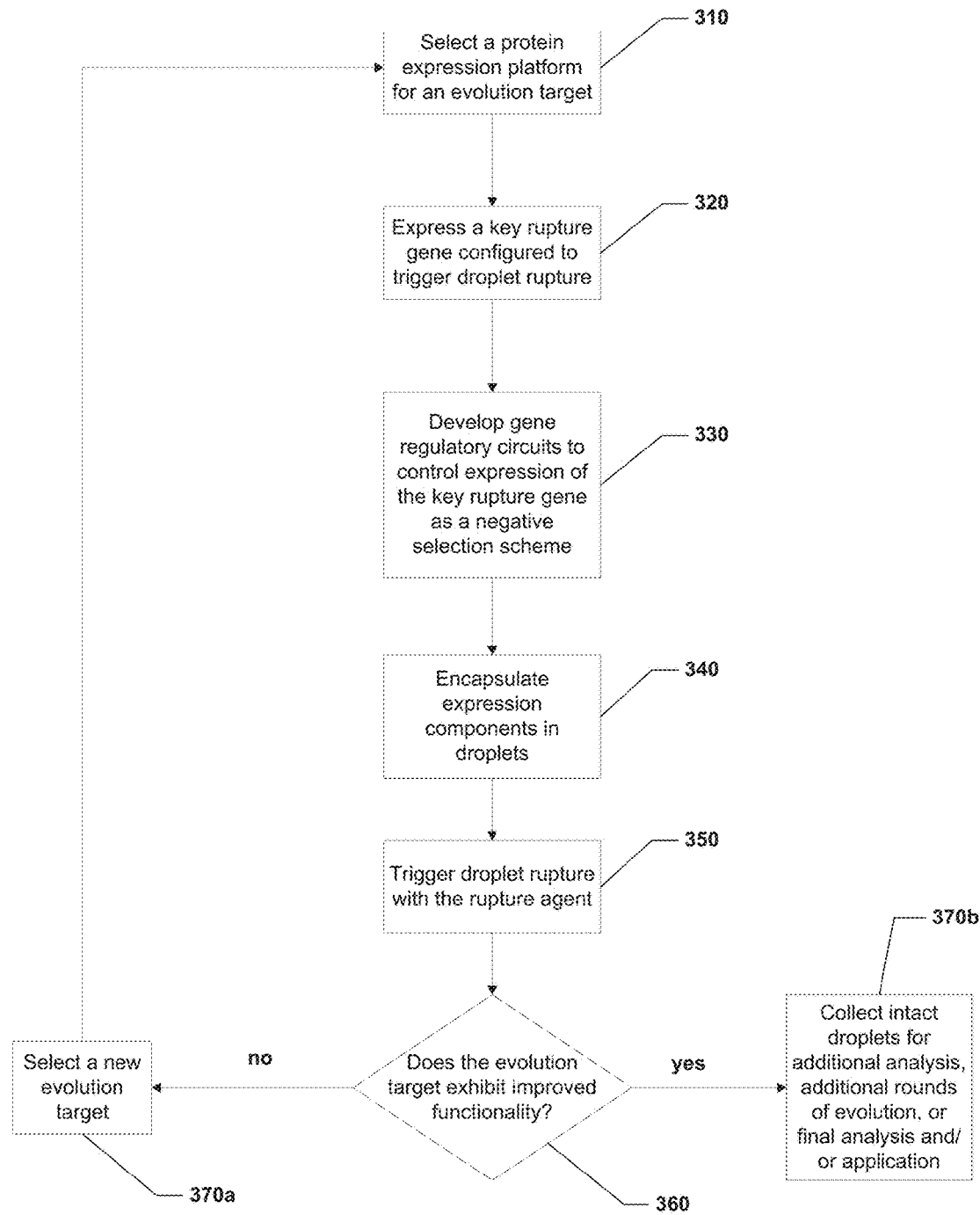
FIG. 5 illustrates a control flow diagram of a negative selection scheme according to an example embodiment.

FIG. 5, for example, illustrates a control flow diagram of a negative selection scheme according to an example embodiment. As shown in FIG. 5, operation may begin by selecting a protein expression platform for an evolution target at operation 310. The operation may continue at operation 320 by expressing a key rupture gene configured to trigger droplet rupture. The operation may continue by developing gene regulatory circuits to control expression of the key rupture gene as a negative selection scheme at operation 330. The operation may continue at operation 340 by encapsulating expression components in droplets. The operation may continue by triggering droplet rupture with the rupture agent at operation 350. The operation may continue at operation 360 by making a decision as to whether the evolution target exhibits improved functionality. If the decision is made that the evolution target does not exhibit improved functionality, then a new evolution target is selected at operation 370a, and the negative selection scheme will begin again starting at operation 310. If the decision is made that the evolution target does exhibit improved functionality, then intact droplets will be collected for additional analysis, for additional rounds of evolution, or for final analysis/application at operation 370b.

EXAMPLES

The present disclosure is further illustrated by the following examples, which in no way should be construed as being limiting. That is, the specific features described in the following examples are merely illustrative, and not limiting.

Engineering Aptamer Biosensors

Riboswitches, i.e. aptamer biosensors, may be developed that silence translation in the absence of chosen analytes. An aptamer sequence will be expressed upstream of a short, random DNA sequence constituting the 5' UTR of the rupture gene within the previously mentioned negative feedback construct. This combination of an aptamer sequence and the 5' UTR constitutes the riboswitch sequence. Riboswitch sequences may then be selected such that rupture is efficient in the presence, but not in the absence of the target analyte. To do this, first, an inducer concentration only slightly above the threshold required to observe rupture for high performing riboswitches within the desired experiment duration will be selected. Next, a series of cells or cell-free expression components, each containing mutated versions of the riboswitch sequence, as well as the gene circuit controlling expression of the rupture agent, will be encapsulated together with the inducer and the target analyte that the riboswitch is to sense. After a period of time, cells or cell-free expression systems in droplets with riboswitch variants that bind the target analyte with high affinity and up-regulate production of the rupture agent will trigger droplet rupture. Ruptured material will be collected and subjected to subsequent negative selection to ensure that droplet rupture was not a consequence of mutations that enable constitutive production of the rupture agent. Specifically, the analyte will be omitted, and the droplet rupture process will be repeated. Only intact droplets will be kept. The DNA from these droplets will be either used to generate a next round of mutants or will be alternatively cloned, purified, sequenced, and further analyzed.

Engineering Protein Switches

A key gene for triggering droplet rupture may be expressed under the control of a promoter that is regulated by the protein switch. Then, protein switch coding sequences would be selected such that rupture is efficient in the presence, but not in the absence of the target ligand. First, the protein switch gene will be placed under inducible control, such that the inducer concentration will be optimized to prevent premature rupture as a function of baseline activity of the protein switch in the absence of the target ligand. In this case, as with the aptamer biosensor example, an inducer concentration that is slightly above the threshold required to observe rupture within the desired experiment duration will be used. The expression components, including either live cells that are transformed with the engineered DNA harboring the protein switch coding sequence or cell-free reagents together with the engineered DNA, inducer, and ligand will be encapsulated. Like the aptamer biosensor example, protein switch variants that exhibit strong responses to the ligand would cause droplet rupture and would be selected. To ensure that activity is not too high in the absence of ligand, negative selection would be performed. Again, this involves omitting the ligand and then only selecting droplets that remain intact. The DNA from these droplets would either be used to generate a next round of mutants or alternatively would be cloned, purified, sequenced, and further analyzed. Ultimately, multiple rounds of positive selection, negative selection, or alternations of positive and negative selection would be performed to evolve switches that exhibit a strong response to ligand addition.

Exemplary Embodiments

Having described various aspects and embodiments of the invention herein, further specific embodiments of the invention include those set forth in the following paragraphs.

In some example embodiments, a method of directed evolution screening is provided. In general, the method of directed evolution screening, according to certain example embodiments, includes selecting a protein expression platform for an evolution target, expressing a key rupture gene configured to trigger droplet rupture, developing gene regulatory circuits to control expression of the key rupture gene as a function of performance of the evolution target, encapsulating expression components in droplets, and triggering droplet rupture by expressing a rupture agent from the key rupture gene. Droplet rupture may be triggered if performance of the evolution target is either satisfactory (positive selection) or unsatisfactory (negative selection). The evolution target may be a rupture gene itself, in which case satisfactory performance is the act of droplet rupture. Alternately, the evolution target may be any gene, in which case, satisfactory performance must be linked to expression of the rupture gene through regulatory circuits. In some embodiments, performance of the evolution target may require external addition of chemical or biological agents. In some embodiments, these external agents may be analytes that are to be sensed by the evolution target. In certain embodiments, external agents may be encapsulated in the droplet or may be able to diffuse into the droplet from the surrounding medium.

In accordance with an example embodiment, selecting a protein expression platform for an evolution target comprises selecting at least one of cells or a cell-free system. In such embodiments, the cells comprise bacterial cells, yeast cells, plant cells, mammalian cells, insect cells, *Aspergillus niger* cells, *Aspergillus oryzae* cells, *Bacillus subtilis* cells, *Corynebacterium glutamicum* cells, *Lactococcus lactis* cells, *Mannheimia succiniciproducens* cells, *Micrococcus luteus* cells, *Streptomyces coelicolor* cells, or *Schizosaccharomyces pombe* cells. In further embodiments, the cell-free system comprises a cell-free system prepared from bacteria, yeast, plant cells, mammalian cells, or insect cells.

In accordance with an example embodiment, expressing a key rupture gene configured to trigger droplet rupture comprises expressing a gene configured for alcohol production. In such embodiments, expressing a gene configured for alcohol production comprises expressing a gene configured for octanol production. In further embodiments, expressing a key rupture gene configured to trigger droplet rupture comprises expressing a gene configured for biosurfactant and/or dispersant production. In such embodiments, expressing a gene configured for biosurfactant and/or dispersant production comprises expressing a gene configured for rhamnolipid production. In other embodiments, expressing a gene configured to trigger droplet rupture comprises expressing at least one of perforins, holins, lysins, or antimicrobial peptides. In such embodiments, expressing at least one of perforins, holins, lysins, or antimicrobial peptides comprises expressing alpha-hemolysin in conjunction with the expression components being encapsulated in liposomes. In certain embodiments, expressing a gene configured to trigger droplet rupture comprises expressing at least one degradative enzyme in conjunction with the expression components being encapsulated in a polysaccharide. In further embodiments, expressing a gene configured to trigger droplet rupture comprises expressing a protease and/or a peptidase in conjunction with the expression components being encapsulated in peptide surfactant vesicle structures. In other embodiments, expressing a gene configured to trigger droplet rupture comprises expressing at least one polymer-degrading enzyme in conjunction with the expression components being encapsulated in polymersomes.

In accordance with an example embodiment, developing gene regulatory circuits comprises developing a positive selection scheme or a negative selection scheme. In certain embodiments, developing a positive selection scheme comprises triggering rupture in response to the evolution target exhibiting a desired functionality. In other embodiments, developing a negative selection scheme comprises avoiding rupture in response to the evolution target exhibiting a desired functionality.

In accordance with an example embodiment, encapsulating expression components in droplets comprises encapsulating at least one of cells or cell-free systems in droplets. In certain embodiments, encapsulating expression components in droplets comprises creating a single emulsion. In such embodiments, a dispersed phase comprises the expression components, and a continuous phase comprises a mixture of oil and surfactant. In other embodiments, encapsulating expression components in droplets comprises creating a double emulsion. In some embodiments, the double emulsion comprises a water-in-oil-in-water (i.e., W/O/W) emulsion having an inner phase, a middle phase, and an outer phase. In such embodiments, the inner phase comprises the expression components, the middle phase comprises oil, and the outer phase comprises an aqueous solution that contains buffers, salts, and/or nutrients. In certain embodiments, the droplets may comprise alginate beads. In such embodiments, the inner phase may comprise at least one of expression components or alginate, the middle phase may comprise oil, and the outer phase may comprise reagents for crosslinking alginate (e.g., calcium chloride or barium chloride). In further embodiments, the droplets may comprise polymersomes. In such embodiments, the inner phase may comprise expression components, the middle phase may comprise at least one of diblock copolymers or homopolymers, and the outer phase may comprise alcohols and/or salts.

In accordance with an example embodiment, the method further comprises identifying rupture efficiency and timing for varying expression strengths of the rupture agent. In such embodiments, identifying rupture efficiency and timing for varying expression strengths of the rupture agent comprises placing the key rupture gene under control of an induction system. In some embodiments, the induction system comprises an inducible cell-free negative feedback circuit.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A method for screening for a genetic variant of a gene that exhibits a predefined function, the method comprising:
    (a) selecting a cell-free protein system for the genetic variant;
    (b) encapsulating the cell-free protein system, a key rupture gene, and expression components in a droplet using a microfluidic device to form an encapsulated reagent, wherein the key rupture gene is any gene configured to trigger droplet rupture and the expression components comprise a plurality of genetic variants of the gene that exhibits a predefined function and a gene regulatory circuit;
    (c) controlling expression of the key rupture gene via the cell-free protein system based on the gene regulatory circuit, wherein the gene regulatory circuit is configured to control expression of the key rupture gene as a function of performance of the genetic variant; and
    (d) screening the encapsulated reagent to determine if the genetic variant exhibiting the predefined function has been produced by selectively causing the key rupture gene to trigger the rupture of the droplet, wherein the expression of the key rupture gene is controlled by the gene regulatory circuit in response to the production of the genetic variant exhibiting the predefined function.

2. The method according to claim 1, wherein the key rupture gene comprises a gene configured for alcohol production.

3. The method according to claim 2, wherein the gene configured for alcohol production comprises a gene configured for octanol production.

4. The method according to claim 1, wherein expressing a key rupture gene configured to trigger droplet rupture comprises expressing a gene configured for biosurfactant and/or dispersant production.

5. The method according to claim 4, wherein expressing a gene configured for biosurfactant and/or dispersant production comprises expressing a gene configured for rhamnolipid production.

6. The method according to claim 1, wherein expressing a gene configured to trigger droplet rupture comprises expressing at least one of perforins, holins, lysins, or antimicrobial peptides.

7. The method according to claim 6, wherein expressing at least one of perforins, holins, lysins, or antimicrobial peptides comprises expressing alpha-hemolysin in conjunction with the expression components being encapsulated in liposomes.

8. The method according to claim 1, wherein expressing a gene configured to trigger droplet rupture comprises expressing at least one degradative enzyme in conjunction with the expression components being encapsulated in a polysaccharide.

9. The method according to claim 1, wherein expressing a gene configured to trigger droplet rupture comprises expressing a protease and/or a peptidase in conjunction with the expression components being encapsulated in peptide surfactant vesicle structures.

10. The method according to claim 1, wherein expressing a gene configured to trigger droplet rupture comprises expressing at least one polymer-degrading enzyme in conjunction with the expression components being encapsulated in polymersomes.

11. The method according to claim 1, wherein the gene regulatory circuit is one of a positive selection scheme or a negative selection scheme.

12. The method according to claim 11, wherein the positive selection scheme comprises triggering rupture of the droplet in response to determining the genetic variant exhibiting the predefined function has been produced.

13. The method according to claim 11, wherein the negative selection scheme comprises avoiding rupture of the droplet in response to determining the genetic variant exhibiting the predefined function has been produced.

14. The method according to claim 1, wherein controlling expression of the key rupture gene of the encapsulated reagent comprises identifying rupture efficiency and timing for varying expression strengths of the key rupture gene.

15. The method according to claim 14, wherein identifying rupture efficiency and timing for varying expression strengths of the key rupture gene comprises placing the key rupture gene under control of an induction system.

16. The method according to claim 15, wherein the induction system comprises an inducible cell-free negative feedback circuit.

* * * * *